(12) United States Patent
Ozdamar

(10) Patent No.: US 8,894,936 B2
(45) Date of Patent: Nov. 25, 2014

(54) PORTABLE CONTAINER WITH AUTOMATIC CARTRIDGE ACTIVATOR, AUTOMATIC VENTILATOR, STERILIZATION SURVEILLANCE WINDOW IN THE STERILIZATION OF ETHYLENE OXIDE WITH GAS DIFFUSION SYSTEM

(76) Inventor: Cem Ozdamar, Bornova/Izmir (TR)

( * ) Notice: Subject to any disclaimer, the term of this patent is extended or adjusted under 35 U.S.C. 154(b) by 101 days.

(21) Appl. No.: 13/641,495

(22) PCT Filed: Jan. 26, 2011

(86) PCT No.: PCT/TR2011/000010
§ 371 (c)(1),
(2), (4) Date: Jul. 2, 2013

(87) PCT Pub. No.: WO2011/133122
PCT Pub. Date: Oct. 27, 2011

(65) Prior Publication Data
US 2013/0272925 A1    Oct. 17, 2013

(30) Foreign Application Priority Data
Apr. 19, 2010  (TR) ................ a 2010 03029

(51) Int. Cl.
*A61L 2/24* (2006.01)
*A61L 2/20* (2006.01)

(52) U.S. Cl.
CPC . *A61L 2/24* (2013.01); *A61L 2/206* (2013.01); *A61L 2202/16* (2013.01)
USPC .................................. 422/117; 422/292

(58) Field of Classification Search
CPC ............................................. A61L 2/24

USPC .................................. 422/117, 292
See application file for complete search history.

(56) References Cited

U.S. PATENT DOCUMENTS

| 3,436,173 A * | 4/1969 | Power ................. 422/116 |
| 3,489,505 A * | 1/1970 | Sonnenschein et al. .... 422/116 |
| 5,209,902 A | 5/1993 | Matthews |
| 5,555,704 A | 9/1996 | Caufield |

FOREIGN PATENT DOCUMENTS

| WO | 9933494 A2 | 7/1999 |
| WO | 2011008178 A1 | 1/2011 |

OTHER PUBLICATIONS

International Search Report for corresponding International Application No. PCT/TR2011/000010.

* cited by examiner

*Primary Examiner* — Sean E Conley
(74) *Attorney, Agent, or Firm* — Egbert Law Offices, PLLC

(57) ABSTRACT

A container with automatic cartridge activator allows automatic activation of the ethylene oxide cartridges and ampoules used in the oxide sterilization peculiar to the gas diffusion system without external human control and intervention and removal of the residual ethylene oxide from the sterilized materials at the end of the sterilization process. The container ensures safe use of the ethylene oxide without posing any danger against human health. The container also eliminates the requirement for use of sterilization bags known as Liner Bag or simply bag, traditionally used in the ethylene oxide sterilization based on gas diffusion system, also allowing instant monitoring of the sterilization conditions inside the container, the sterilization cell, from outside of the system.

8 Claims, 2 Drawing Sheets

PORTABLE CONTAINER WITH AUTOMATIC CARTRIDGE ACTIVATOR, AUTOMATIC VENTILATOR, STERILIZATION SURVEILLANCE WINDOW IN THE STERILIZATION OF ETHYLENE OXIDE WITH GAS DIFFUSION SYSTEM

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The current invention aims at taking away the residual ethylene oxide over a container and sterilized materials and substances by ensuring that portable containers in shape of a metal bin is used instead of membrane-structured sterilization bags of generally polyethylene alloy, also known as Liner Bag or Bag used in the sterilization of ethylene oxide, a practice peculiar to the gas diffusion system; that the ethylene oxide cartridges used in the gas diffusion systems of the said containers at the same time are automatically activated without external intervention and that the sterilized materials and substances within the container are automatically ventilated at the end of the process of sterilization.

2. Description of Related Art Including Information Disclosed Under 37 CFR 1.97 and 37 CFR 198

The current known technique of gas diffusion ethylene oxide sterilization underlines that the medical equipments are put into the sterilization bag that has membrane structured sterilization bag made of polyethylene compound which is also known as liner bag in naked or packaged form together with ethylene oxide ampoule or cartridge. After the said, bag is sealing by means of connection or thermal methods (preferably by adding moisturizer [humidity chip] and dosimeter), the ampoule or the ampoule in the cartridge is broken by hand for activation. At this stage, there is a porous membrane bag that could be easily holed or torn down between and is in 10-20 micron thickness between the gas and the user. The sterilization is carried out by putting the bag which includes these materials and cartridge either in the environment or into sterilizer cabinets with gas diffusion technique generally used for this operation, with the bag being closed. At the end of the sterilization process, the bag is unseated by use of hand or tearing it front its edge by means of a sharp apparatus to make sure that the ethylene oxide inside the bag is released. Because this is a harmful gas, the user health is strongly affected by the release during the activation and bag ventilation.

There is no application whatsoever to request a grant for patent or license filed with the relevant authorized institution similar to the current invention under review featuring a container with automatic cartridge activator that uses gas diffusion technique in ethylene oxide sterilization process.

To sum, the existence of the need for a container with automatic cartridge activator that eliminates the above mentioned drawbacks and disadvantages in the sterilization of ethylene oxide that has gas diffusion technique, and the inadequacy of the existing solutions make creation of a new method a necessity.

BRIEF SUMMARY OF THE INVENTION

Based on the current status of the technique, it could be said that the purpose of the invention is to develop a portable container with an automatic cartridge activator and automatic ventilator in shape of a metal bin for a safer use of ethylene oxide without posing any danger against human health instead of thin membrane-structured sterilization bags in 10-20 micron thickness that could be easily torn down with a polyethylene compound—also known as Liner Bag or simply Bag—at the ethylene oxide sterilization processes with gas diffusion system.

Another goal of the invention is to develop an automatic activator container compatible with every type of cartridges in current use in all related systems and to attain high level of security in all relevant systems.

The invention also seeks to ensure that the advantages of the system are effectively benefited by increasing the amount of ethylene oxide sterilization with gas diffusion technique subsequent to the heightened security and safety.

To attain the said goals, a container was invented with respect to the gas diffusion technique ethylene oxide sterilization.

Any mechanism where the invention is to be used includes a metal container, main body and cover as well as an impermeability gasket.

A preferred version of the invention is developed in a way to feature an automatic activator container inclusive of some space that could host the gas cartridge inside the container, a filtered ventilator hole against bacteria, an internal rechargeable battery that would ensure electrical operation, a turn-on and off switch that controls the operation, led lamps displaying the status of battery power, a mini speaker able to warn the user audibly, a mini dc gear electrical motor that ensures the activation of the cartridge, motor mil and piston, receiver-transmitter unit that ensures wireless operation of the activator during the workout, the temp probe that measures the temp info, a chemical indicator (dosimeter) surveillance window that allows instant monitoring of the sterilization conditions from outside.

Another preferred version of the invention also features an electronic card that ensures the entire operation and control. The system also includes an optional digital electronic info screen that could be seen from outside of the container and allows communication between the machine and the user. The digital screen allows view of the remaining time, battery power status and other relevant information. At the same time, optionally, the screen may be touch-operated and allows entrance of commands from the screen. It also includes a mini speaker to warn the operator and give information.

Another preferred version of the invention uses a ventilation valve operated by an internal electrical motor for operation. The ventilation valve is coupled with the ventilation channel and connects the inside of the container to the outside.

A preferred version of the invention also uses an electrical switch that allows the various type startup and shut down of the device, a connector for charging the battery, optionally led lamps displaying the battery power status that could be viewed from outside of the container, a mini receiver helping for wireless operation and communication, a conveyor allowing transport of the container and a sensor that detects the presence of the cartridge and lamp.

A preferred version of the invention also allows use of portable container as a fixed type inside the sterilizer via the external connecting inlets.

A preferred version of the invention also includes sections over the activator where the humidifier and dosimeter indicators could be placed.

The relevant figures on "Portable container with automatic cartridge activator, automatic ventilator, sterilization surveillance window in the sterilization of ethylene oxide with gas diffusion system" invented to attain the elaborated goal are attached:

REFERENCE NUMBERS

Figure 1:
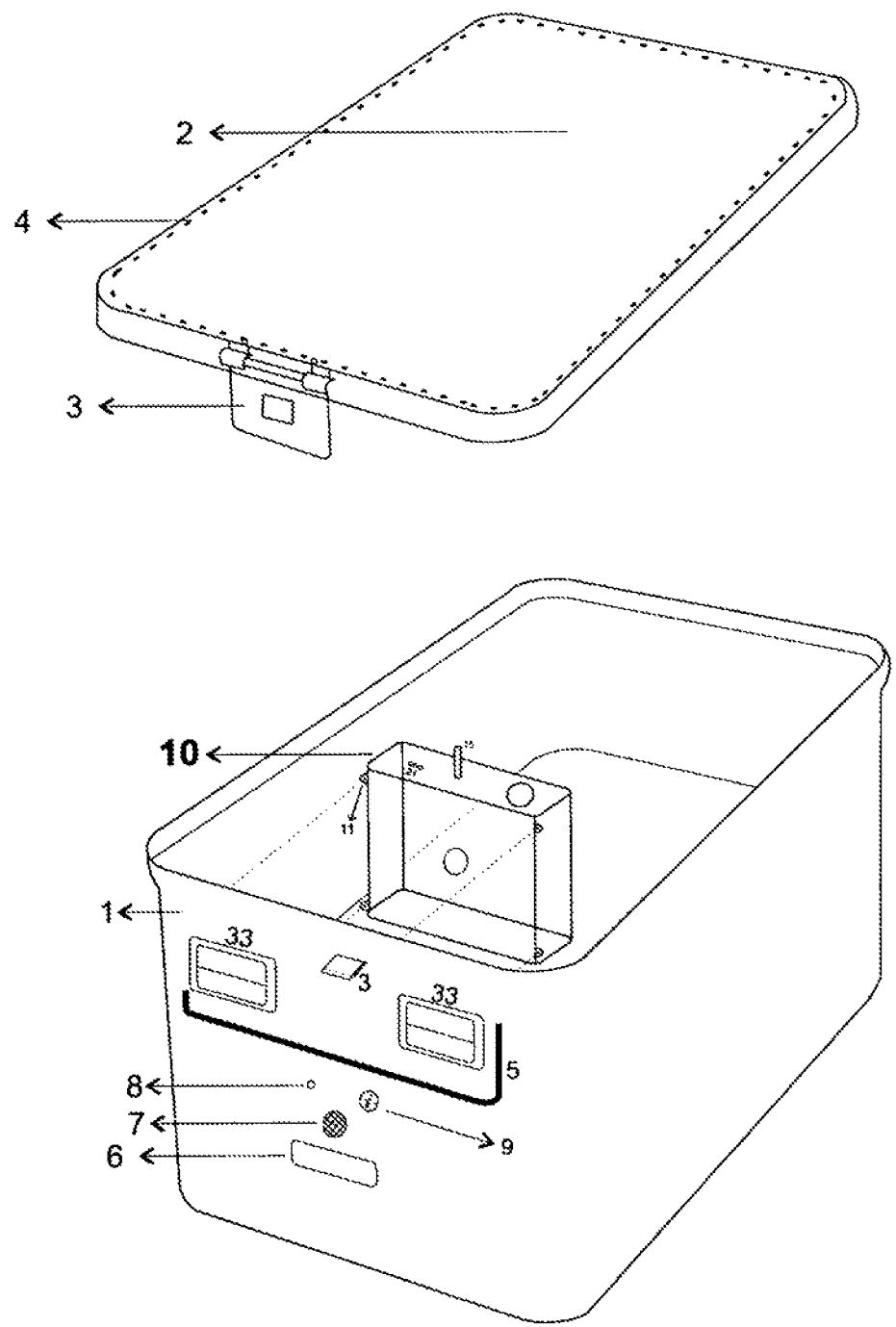
FIG. 1 depicts the overall outlook of the automatic cartridge activator container.
Figure 2:
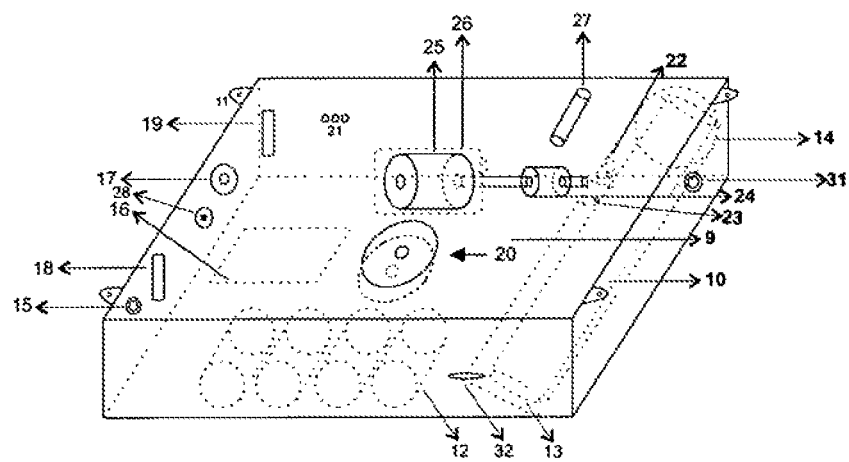
FIG. 2 provides the details of the automatic cartridge activator inside the container.
Figure 2:
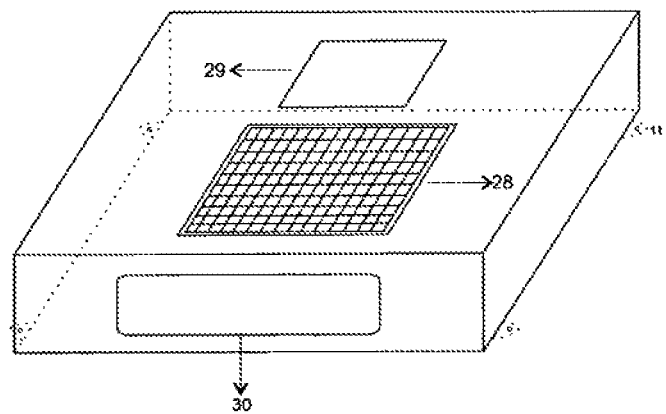

1. Container body
2. Container cover
3. Container seal
4. Impermeability gasket
5. Container conveyor
6. Sterilization surveillance window and transparent cover
7. Ventilation input with bacteria, filter
8. Operation status led
9. Turn on-off switch
10. Automatic cartridge activator
11. Automatic cartridge activator connection tips
12. Batteries
13. Ethylene oxide cartridge/ampoule
14. Ampoule/Cartridge hole
15. Connector for battery charge
16. Electronic card
17. Mini speaker/Buzzer
18. Wireless receiver-transmitter
19. Temperature probe
20. Ventilation valve
21. Battery power status fed
22. Limit switch
23. Spring Bali of Cartridge Fixing
24. Drive piston and Rod
25. DC gear motor
26. Motor base and mechanism
27. Safety pin
28. Humidifier hole
29. Electronic screen
30. Sterilization indicator slot
31. Gas outlet channel
32. Cartridge sensor
33. Labeling slot

DETAILED DESCRIPTION OF THE INVENTION

Basically the system consists of a container body (1), container cover (2) and integrated automatic cartridge activator (10) inside the container body. The goods to be sterilized are placed inside the container in packaged or naked condition. They are further put into either the slots (14) for ethylene oxide cartridge and ampoule (13). Preferably, the sterilization status indicator is added the slot (30) behind the sterilization surveillance window with a transparent cover (6). Preferably a humidifier put into the slot (28). After the container cover (2) is closed, the on-off button of automatic activator (9) is pressed; with the receipt of the operation signal from the mini speaker (17), the operation status led (8) is activated. At the same time, if available, at a digital screen (29) that could be seen from outside and used optionally, the remaining time is displayed via a timer following a series of operation messages. During this period, the operator places the automatic cartridge activator container inside the sterilizer with gas diffusion technique or a remote safe place where the sterilization process could be performed. When little time remains before the activation, the mini speaker (17) gives a warning. When the remaining time is over, the trigger motor (25) moves the trigger piston (24) towards the cartridge. During this movement, the ventilation valve (20) connected to the piston (25) shuts down. The moving piston (24) ensures thanks to the force applied to the ethylene oxide cartridge that cover cap drilled/ampoule is broken and the gas inside is released and that the activation is performed. The gas come out of the gas output channel (31) and fills in the container. The movement rate of the piston is determined in the direction of the electronic card (16) via limitation of the time and limit switches (22) depending on the software inside.

When the sterilization process is completed, the on-off button (9) is pressed to take the mechanism to another position. This time, the drive piston (24) retreats and the ventilation valve (20) connected to the piston is opened up; in this way, the waste gas inside the container is released and fresh air is taken inside the container.

Owing to the sterilization surveillance window (6), the sterilization process inside the container may be monitored without having to open up the container cover from the outside by use of a special sterilization indicator.

The status of the batteries inside the automatic cartridge activator (12) may be monitored via power status led (21). The power status can be communicated to the digital screen (19), if so desired. The batteries can be charged via charger connector (15).

The wireless communication, transmitter and receiver (18) connected to the electronic card (16) allows joint operation in the sterilizer body by use of signals coming from outside. The internal temp probe (19) allows control of the cartridge activation via the information on procured temperature.

The safety pin (27) disallows operation while the container cover is open.

The cartridge sensor (32) disallows operation while there is no cartridge.

At the input and output of the ventilation channel (7), there is a bacteria filter to prevent clogging by undesired substances and entrance of bacteria.

Labeling process is performed by use of labeling slots (33) outside the container by addition of various labels.

The invention claimed is:

1. A container apparatus for use with ethylene oxide cartridges for ampules that are used in ethylene oxide sterilization in a gas diffusion system without human touch and with automatic ventilation of sterilized materials in the gas diffusion system at the end of the sterilization so as to ensure removal of residual ethylene oxide from the sterilized materials, the container apparatus comprising:
    a container body;

a container cover removably positionable on said container body;
an automatic cartridge activator positioned within said container body;
a slot formed in said automatic cartridge activator whereby the cartridge or ampule can be placed within said automatic cartridge activator;
a ventilation channel formed on said container body, said ventilation channel having a bacteria filter;
an internal battery cooperative with said automatic cartridge activator so as to provide electricity to said automatic cartridge activator;
an on/off switch cooperative with the automatic cartridge activator so as to control an on or off operation of said automatic cartridge activator;
a mini DC electrical gearmotor positioned in said automatic cartridge activator;
a drive piston and rod positioned in said automatic cartridge activator, said drive piston and rod being movable toward the cartridge or ampule by said mini DC electrical gearmotor so as to break a seal to break the cartridge or ampule;
a ventilation valve connected to the piston so as to close during movement of the piston and to open when the piston retreats;
an electronic card suitable for controlling operation of said drive piston and rod;
a cartridge sensor positioned in said automatic cartridge activator so as to sense for a presence of the cartridge or ampule;
a safety pin cooperative with said container cover so as to disallow lower opening of the upset automatic cartridge activator when the cover is opened;
a gas outlet channel formed in said automatic cartridge activator so as to allow gas to be released after the breaking of the cartridge or ampule;
an impermeability gasket integrated onto said container cover;
a sterilization surveillance window having a transparent cover;
a sterilization status indicator placed over said container body;
a labeling slot formed on said container body;
an operation status lamp positioned on said container body;
LED lamps cooperative with said internal battery so as to be indicative of a battery power status;
a mini speaker positioned on said automatic cartridge activator so as to provide a sound warning to a user; and
a humidifier slot formed in said automatic cartridge activator and suitable for the receipt of a humidifier therein.

2. The container apparatus of claim 1, said container body and said container cover being configured with said automatic cartridge activator so as to activate the cartridge or ampule without human touch.

3. The container apparatus of claim 1, said container body having no gas diffusion bag therein, said automatic cartridge activator having no gas diffusion bag connected thereto.

4. The container apparatus of claim 1, said container body being portable.

5. The container apparatus of claim 1, said container body suitable for allowing instant monitoring of sterilization conditions within said container body from outside said container body.

6. The container apparatus of claim 1, said ventilation valve allowing automatic ventilation of an interior of said container body and said automatic cartridge activator.

7. The container apparatus of claim 1, said container body further comprising:
   a connector cooperative with said internal battery so as to allow for a charging of said internal battery;
   a receiver/transmitter unit cooperative with said automatic cartridge activator so as to allow for wireless communication with said automatic cartridge activator;
   a temperature probe cooperative with an interior of said container body so as to measure temperature therein;
   a screen provided on said automatic cartridge activator so as to provide control information; and
   operation limit switches cooperative with said automatic cartridge activator so as to control and limit the operation of said automatic cartridge activator.

8. The container apparatus of claim 7, said container apparatus being fixed within a sterilizer by external connection slots.

* * * * *